United States Patent
Amblard

(10) Patent No.: US 7,890,168 B2
(45) Date of Patent: Feb. 15, 2011

(54) ACTIVE IMPLANTABLE MEDICAL DEVICE OF AAI/DDD TYPE, NOTABLY CARDIAC PACEMAKER, COMPRISING MEANS FOR AUTOMATIC MODE ADJUSTMENT AT THE IMPLANTATION

(75) Inventor: Amel Amblard, Chatenay-Malabry (FR)

(73) Assignee: ELA Medical S.A.S., Montrouge (FR)

( * ) Notice: Subject to any disclaimer, the term of this patent is extended or adjusted under 35 U.S.C. 154(b) by 916 days.

(21) Appl. No.: 11/614,733

(22) Filed: Dec. 21, 2006

(65) Prior Publication Data

US 2007/0162078 A1    Jul. 12, 2007

(30) Foreign Application Priority Data

Dec. 21, 2005    (FR) ................................. 05 13022

(51) Int. Cl.
*A61N 1/372* (2006.01)
(52) U.S. Cl. ................................ 607/9; 607/14; 607/15
(58) Field of Classification Search .................... 607/9, 607/14, 15
See application file for complete search history.

(56) References Cited

U.S. PATENT DOCUMENTS

| | | | |
|---|---|---|---|
| 5,318,594 A | 6/1994 | Limousin et al. |
| 5,476,485 A | 12/1995 | Weinberg et al. |
| 6,154,675 A | 11/2000 | Juran et al. |
| 6,343,231 B1 | 1/2002 | Bouhour et al. |
| 2004/0010292 A1 | 1/2004 | Amblard et al. |
| 2004/0220625 A1 | 11/2004 | Silvestri et al. |
| 2005/0143780 A1 | 6/2005 | Henry et al. |

FOREIGN PATENT DOCUMENTS

| | | |
|---|---|---|
| EP | 0488904 | 11/1991 |
| EP | 1050320 | 11/2000 |
| EP | 1346750 | 9/2003 |
| EP | 1438985 | 7/2004 |
| EP | 1550480 | 7/2005 |

*Primary Examiner*—Scott M Getzow
*Assistant Examiner*—Joseph M Dietrich
(74) *Attorney, Agent, or Firm*—Orrick Herrington & Sutcliffe, LLP

(57) ABSTRACT

An active implantable medical device of the AAI/DDD type, notably a cardiac pacemaker, including automatic mode adjustment at implantation. The device detects spontaneous atrial and ventricular events, and is able to pace the atrium and ventricle. The device can operate in an AAI mode with ventricular sensing, a DDD mode, and includes automatic mode commutation, able to schedule, as a function of predetermined criteria, commutation from AAI to DDD mode, and reversely from DDD to AAI. The device automatically detects an implantation and has its initial mode of operation adjusted upon detection of the implantation (10). The device temporarily operates (14) in an AAI mode with activation of the means for mode commutation, then analyzes (20) the atrio-ventricular conduction so as to detect whether a potential conduction disorder exists. In case of a potential conduction disorder existing (presence) (24), the device is then set to a DDD mode and the automatic mode commutation is inhibited. Otherwise (26), the device is set to an AAI mode, and the automatic mode commutation remains activated.

14 Claims, 1 Drawing Sheet

ACTIVE IMPLANTABLE MEDICAL DEVICE OF AAI/DDD TYPE, NOTABLY CARDIAC PACEMAKER, COMPRISING MEANS FOR AUTOMATIC MODE ADJUSTMENT AT THE IMPLANTATION

FIELD OF THE INVENTION

The present invention relates to "active implantable medical devices" as such devices are defined by the Jun. 20, 1990 Directive 90/385/CEE of the Counsel of the European Community, and more particularly to "multisite" (triple or quadruple chamber) pacemakers, defibrillators and/or cardioverter devices that are able to monitor heart activity and to deliver to the heart electrical pulses intended to provide pacing, resynchronization, cardioversion and/or defibrillation in response to a diagnosis of a cardiac rhythm disorder. The invention is more particularly related to those devices that are equipped with pacing and sensing circuits associated with the atrium and the ventricle, and can operate according to one of two known operating modes, DDD and AAI (the AAI mode being a DDD mode having a lengthened atrio-ventricular delay). These devices also are preferably equipped with a mode called "DDD-AMC" or "AAISafeR" ensuring an automatic mode commutation ("AMC") or switching from DDD to AAI and conversely.

BACKGROUND OF THE INVENTION

The basic operating mode of a DDD/AAI pacemaker is in the AAI mode—or more precisely a "pseudo-AAI" mode—with a single chamber atrial pacing (AAI mode stricto sensu), and a monitoring of ventricular activity. This operating mode is maintained as long as atrio-ventricular conduction is normal, that is, as long as each atrial event (either an atrial detection, corresponding to a spontaneous activity, or an atrial stimulation) is followed by an associated ventricular detection.

In certain circumstances, however, atrio-ventricular blocks (AVB) may appear, leading to a temporary disorder of the depolarization of the ventricle. In this case, as long as several conditions are met, the pacemaker automatically commutes to an automatic DDD mode, with parameters that are optimized for this situation involving a temporary AVB. After the disappearance of the AVB, and therefore after a re-establishment of atrio-ventricular conduction, the pacemaker automatically commutes back to AAI mode, as long as several other conditions of operation are met.

This principle of operation allows maintaining a spontaneous ventricular activity, for patients presenting an atrio-ventricular that is, most of time, normal.

Such a commutation between DDD and AAI operating modes is notably described in EP-A-0488904 and its counterpart U.S. Pat. No. 5,318,594 (commonly assigned herewith to ELA Medical), and EP-A-1346750 and its counterpart U.S. Published Patent application 2004/010292 (also commonly assigned to ELA Medical), which disclose the manner in which AVBs are detected and trigger the mode commutation and the AAISafeR mode operation, which disclosure is incorporated herein by reference in its entirety.

The present invention is based upon some observations made while actually following up patients, a short while after they were implanted with a device having the aforementioned "AAISafeR" feature (i.e. DDD/AAI device with automatic mode commutation).

Indeed, such devices are parameterized during their manufacturing process, either in automatic DDD mode (with no mode commutation), or in DDD/AAI with automatic mode commutation (i.e., with the "AAISafeR" feature activated). It is thus left to the practitioner to modify, if need be, the standard programming at the implantation, as a function of the patient's specific pathology.

However, for devices programmed with AAISafeR feature on, the absence of reprogramming by the practitioner may lead to side effects in certain patients for which such reprogramming would be necessary.

Indeed, before the implantation, the device only comprises the pulse generator, which is not yet equipped with adequate leads. The lead being not yet connected, the device will not detect any atrio-ventricular conduction (no ventricular signal is collected, as the lead is not yet connected). If the AAISafeR feature is on, that will induce a commutation to the DDD mode, which will be first temporary, then prolonged with a periodic test so as to allow a commutation back to AAI. This test is run after a relatively long delay after commutation towards DDD mode, so as to prevent commutations from AAI to DDD and then from DDD to AAI happening too quickly.

Thus, for those patients implanted in this manner, the AAISafeR mode allows a commutation back to AAI if the device detects a sustained ventricular activity, or after the periodic test that will be executed regularly, typically every morning.

Also, such a test, that is specific to the AAISafeR feature, makes sense only for patients having a permanent or quasi-permanent atrio-ventricular conduction.

On the other hand, for patients having a confirmed permanent atrio-ventricular block, such a test, which generates long ventricular cycles while tolerating the absence of ventricular activity over a limited period of time, is not appropriate. It can even be noxious, by creating in certain vulnerable patients some conditions favorable to the apparition of other disorders, which are very important to minimize, if not prevent.

OBJECTS AND SUMMARY OF THE INVENTION

It is, therefore, an object of the present invention to overcome this hindrance, by proposing a device that automatically adapts, at the moment of the implantation, the programming of automatic mode commutation (i.e., on or off), in the most appropriate manner for the patient's heart pathology, notably according to whether the natural atrio-ventricular conduction is preserved.

To that end, the invention is broadly directed to coupling the AAISafeR feature to a feature of automatic detection of the implantation. That detection is, for example, described in European published patent application EP-A-1,438,985 and its US counterpart published patent application US 2004/0220625, commonly assigned herewith to ELA Medical, which discloses a device that is able to analyze the shape characteristics of the pulses collected on the various terminals of the pulse generator, and deduce therefrom whether or not this device is equipped with a lead, and whether the lead has been introduced in the implantation site, that is, within the incision or "pocket" in which the surgeon has looked into implanting it.

One aspect of the invention is therefore directed to a device of a general type, known as such, comprising: means for detection of spontaneous atrial and ventricular events, means for delivering ventricular and atrial pacing, means able to operate the device in DDD mode, means for mode commutation able to schedule, as a function of predetermined criteria, a commutation from AAI mode to DDD mode and reversely the commutation from DDD mode back to AAI mode.

In a manner characteristic of the invention, the device further comprises means for automatic detection of the implantation, and means for an initial adjustment of the mode, activated upon detection of the implantation through said automatic implantation detection means. The means for initial mode adjustment preferably comprises means for successively: operating the device in AAI mode with ventricular sensing and activation of mode commutation means; analyzing the atrio-ventricular conduction so as to detect a potential conduction disorder; in case of detected conduction disorder, switching the device to DDD mode and inhibiting the means for mode commutation; in case of the absence of detected conduction disorder, maintaining or switching the device to the AAI mode with ventricular sensing and activating the means for mode commutation.

The means for initial mode adjustment also may establish an index, stored in the device's permanent memory, selectively as a function of the presence or absence of detected conduction disorder.

Advantageously, a delay is applied upon activation of the means for initial mode adjustment, after detection of the implantation.

The means for analysis of atrio-ventricular conduction may notably comprise means for determining the presence of a conduction disorder when, over a predetermined period of time or a predetermined number of heart cycles, the number of mode commutations from AAI to DDD exceeds a first predetermined threshold, or the percentage of paced ventricular cycles exceeds a second predetermined thresh-old. Preferably, this analysis is operated by excluding from the predetermined period of time or predetermined number of heart cycles, the periods with presence of atrial and ventricular rhythm disorders, the phases of sinusal tachycardia above a predetermined value of heart rate, and the phases of exercise identified by physiologic sensors.

Another aspect of the present invention is directed towards a method for initiating the pacing mode of an active implantable medical device of the cardiac pacemaker, defibrillator and/or cardioverter type, in a device able to deliver pacing pulses to an atrium and a ventricle and having an AAI mode of pacing, a DDD mode of pacing, and an automatic mode commutation for switching pacing between AAI and DDD modes. One such method comprises automatically detecting an implantation of the device in a patient; temporarily operating the device in an AAI pacing mode with automatic mode commutation upon a detected implantation; detecting spontaneous atrial and ventricular events including atrio-ventricular conduction, in response to said detected implantation; analyzing the atrio-ventricular conduction and determining whether a potential atrio-ventricular conduction disorder exists, and providing an initial mode of operation subsequent to said temporary operating mode in response to said detected implantation, wherein said initial mode of operation is selected from among an AAI mode with ventricular sensing and an active automatic mode commutation in response to an absence of a detected potential conduction disorder, and a DDD mode with an inactive automatic mode commutation in response to a presence a detected potential conduction disorder.

BRIEF DESCRIPTION OF THE DRAWINGS

Further features, characteristics and advantages of the present invention will become apparent to a person of ordinary skill in the art from the following detailed description of a preferred embodiment of a device of the present invention, made with reference to the annexed FIGURE which is a diagram representing the different steps implemented by a device of the invention.

DETAILED DESCRIPTION OF THE INVENTION

Figure 1:
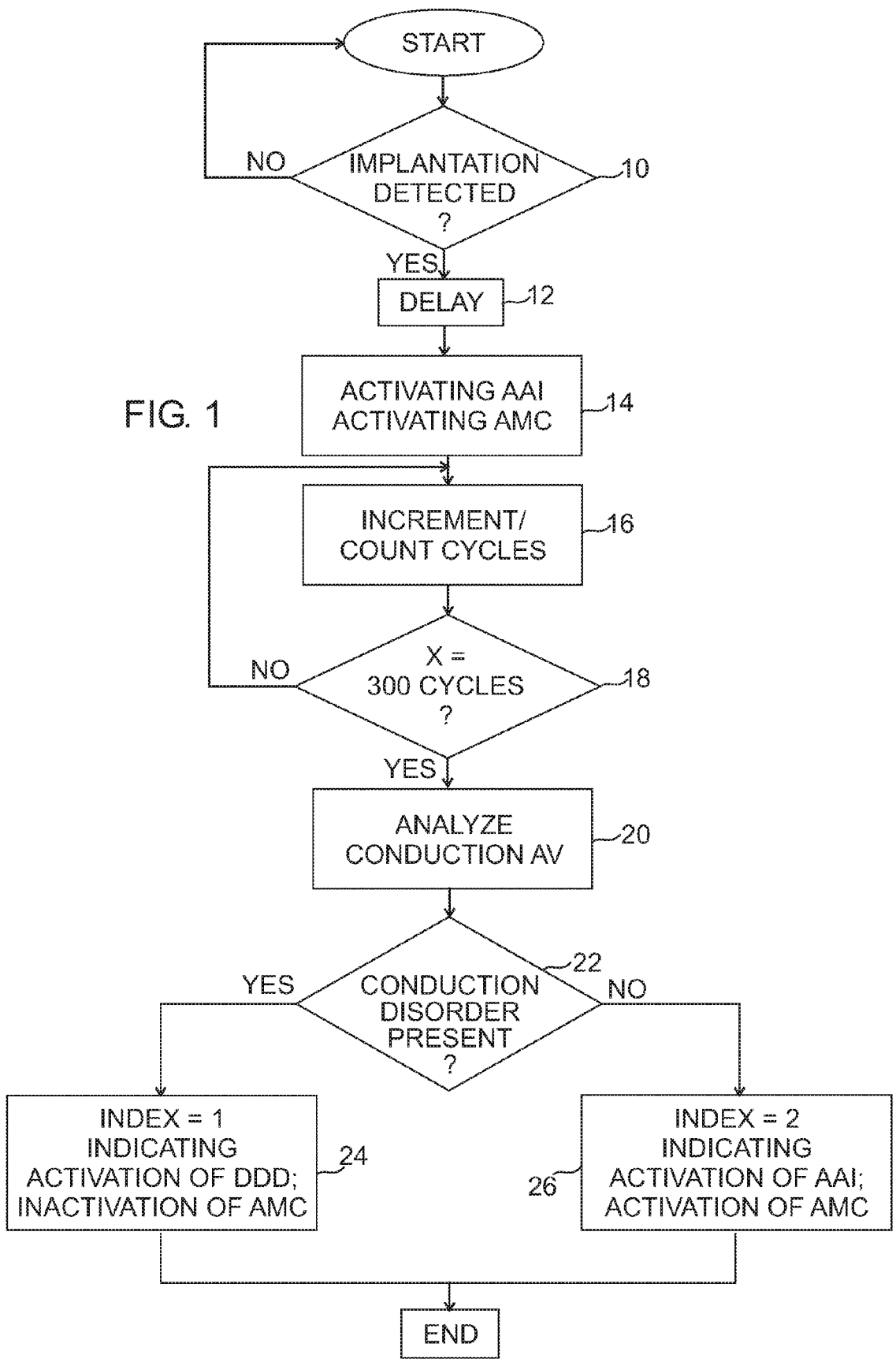

Regarding the software-related aspects thereof, the present invention can be implemented by an appropriate programming of the software of a known active implantable device, for example, a device of the pacemaker type, or of the defibrillator/cardioverter type, including means of acquisition of a signal conveyed by endo-cardial leads and/or several implanted sensors. The invention can notably be applied to the implantable devices marketed by ELA Medical, Montrouge, France, such as the Symphony and ELA Rhapsody brand pacemakers, and the Alto and Ovatio brand defibrillators.

These devices are equipped with programmable microprocessors, including circuits intended and able to acquire, format and process electrical signals collected by implanted electrodes, and deliver pulses to these electrodes according to defined cardiac control algorithms for selectively delivering pacing, cardioversion and/or defibrillation pulses. It is also possible to upload towards these devices already implanted, by telemetry, software routines that will be stored in internal memory and run so as to implement the function/features of the present invention, as described in more detail below. Implementing the functionality of the present invention into these devices is a manner of implementation that is believed to be easily feasible by and within the abilities of a person of ordinary skill in the art, and will therefore not be described in detail in this document.

First of all, the device (step 10) detects whether the implantation has been performed with reference to the drawing. That detection is operated through various known techniques, for example, through the analysis of shape characteristics of the pulses collected on the pulse generator terminals, as disclosed in EP-A-1,438,985 and its US counterpart US 2004/0220625 recited above, to which reference is made. That detection can equally be operated through other techniques, notably through scrutinising the generator's battery consumption. These detection techniques allow detection of not only the connection of a lead to the generator and the type of lead (unipolar or bipolar), but also the effective implantation, that is: the introduction of the pulse generator, equipped with its lead, within the implant the device, a site (incision or "pocket") in which the surgeon has sought to implant the device, a configuration in which the case is in contact with the patient's tissues and may serve as a reference potential.

Where these conditions are fulfilled (lead connection and effective implantation), the device can be switched on so as to be completely operational.

Advantageously, this activation is not operated immediately, but rather after a delay (step 12) has elapsed, in order to prevent interference from the surgical environment to affecting the patient's heart rhythm or the collected signals, and to take into account a potential readjustment by the practitioner, of the pulse generator within its implantation pocket, which could have the effect of temporarily interrupting the contact with the patient's tissues. This delay, which may last up to 2 hours after initially detecting an implantation, for instance, is however optional. It can be programmed by the manufacturer, or by the implanting practitioner.

The following step 14 concerns rendering the device functional, by activating the "AAISafeR" feature, that is by putting the device in AAI mode, and activating the automatic mode commutation (independently from the initial device configuration, either DDD or AAISafeR, which is done by the manufacturer).

In the beginning, the operation of the pulse generator is temporarily placed in AAI mode with a surveillance of ventricular activity: the algorithms search for the presence or absence of ventricular activity, which in the latter case would give suspicion of an AVB, so as to eventually commute to dual chamber pacing DDD mode with atrio-ventricular association, i.e. with calculation and application of an atrio-ventricular delay for controlled pacing of the ventricle.

In order to render this search more reliable, the analysis shall be made under stable sinusal conditions, at rest. Consequently, the period of analysis (either a number of cycles or a time period) excludes the periods in atrial or ventricular rhythm disorder, in sinusal tachycardia over a predetermined rate (typically 100 bpm) or in exercise phase, such a phase being, for example, determined by means of physiologic sensors.

After a certain number of operating cycles in slow sinusal rhythm, for example 1500 cycles, or after a given period of time, for example 15 minutes (steps 16 and 18), the device operates an analysis of atrio-ventricular conduction (step 20). That analysis can be operated through any of a number of known algorithms, notably:

counting the number of AAI/DDD commutations since the activation of AAISafeR feature, or counting, over that same duration, the number of cardiac cycles with paced ventricular rhythm.

If the number of AAI/DDD commutations exceeds a threshold S1, or if the percentage of cycles with ventricular pacing exceeds a given threshold S2, then the device concludes that there is a conduction disorder; in the contrary case, it concludes the absence of such a disorder.

The final programming of the pacing mode comes once the result of this analysis of atrio-ventricular conduction is obtained (step 22):

in the presence of a conduction disorder (step 24), the pacing mode that will be applied to the patent is permanent DDD mode, with automatic mode commutation switched off. An index is set at the value "1".

In the absence of conduction disorder (step 26) the AAISafeR feature is fully activated, that is the device is set to AAI mode with automatic mode commutation AMC switched on; the index is set to the value "2".

The index thus provides a message to the attending practitioner when following up with the patient for the first time after implantation, that message being for instance:

"the device is operating in DDD mode due to the AV conduction disorders your patient presented at the implantation" (if the index value is "1"), or "the device is operating in AAISafeR mode because your patient presented a preserved AV conduction at the implantation" (if the index value is "2")

One skilled in the art will appreciate that the foregoing invention may be practiced by other than the embodiments described, which are disclosed for purposes of illustration and not of limitation.

I claim:

1. An active implantable medical device of a cardiac pacemaker, defibrillator and/or cardioverter comprising:

means for detecting spontaneous atrial and ventricular events including atrio-ventricular conduction;

means for mode commutation conditionally commutating between an AAI mode with ventricular sensing and a DDD mode;

means for automatic detection of implantation;

means for mode adaptation activated over a period of adaptation after detecting implantation by said means for automatic detection of implantation, said means for mode adaptation temporarily operating the device in said AAI mode and sensing a ventricular activity signal over the period of adaptation; and means for analyzing the ventricular activity signal sensed over the period of adaptation to detect a conduction disorder over the period of adaptation, wherein the means for mode adaptation determines pacing mode of the device after the period of adaptation by, in a presence of the conduction disorder, setting the device in the DDD mode and inhibiting the means for mode commutation, and in an absence of the conduction disorder, setting the device in the AAI mode with ventricular sensing and activating the means for mode commutation.

2. The device of claim 1, wherein the device further comprises a memory and wherein the means for mode adaptation sets an index and stores the index in the memory of the device, selectively as a function of the presence or the absence of the conduction disorder.

3. The device of claim 1, wherein the means for mode adaptation delays the period of adaptation after detecting implantation by the means for automatic detection of implantation.

4. The device of claim 1, wherein the means for analyzing the atrio-ventricular conduction determines the presence of the conduction disorder when, over a predetermined period of time or a predetermined number of heart cycles, the number commutations between the AAI mode and the DDD mode exceeds a first predetermined threshold.

5. The device of claim 4 further comprising a physiologic sensor, wherein said means for analyzing the atrio-ventricular conduction analyzes the atrio-ventricular condition by excluding from said predetermined period of time or said predetermined number of heart cycles, periods of the conduction disorder, phases of sinusal tachycardia beyond a predetermined value of heart rate, and phases of exercise identified by means of the physiologic sensor.

6. The device of claim 1, wherein the means for analyzing the atrio-ventricular conduction determines the presence of the conduction disorder when, over a predetermined period of time or a predetermined number of heart cycles, the percentage of paced ventricular cycles exceeds a second predetermined threshold.

7. The device of claim 6 further comprising a physiologic sensor, wherein, said means for analyzing the atrio-ventricular conduction analyzes the atrio-ventricular condition by excluding from said predetermined period of time or said predetermined number of heart cycles, periods of the conduction disorder, phases of sinusal tachycardia beyond a predetermined value of heart rate, and phases of exercise identified by means of the physiologic sensor.

8. A method for determining pacing mode of an active implantable medical device of the cardiac pacemaker, defibrillator and/or cardioverter comprising:

detecting an implantation of the device in a patient;

temporarily operating the device in an AAI mode with automatic mode commutation and sensing a ventricular activity signal over a period of adaptation after detecting implantation;

detecting spontaneous atrial and ventricular events including atrio-ventricular conduction;

analyzing the ventricular activity signal sensed over the period of adaptation and determining whether a conduction disorder exists over the period of adaptation;

determining the pacing mode of the device after the period of adaptation by setting the pacing mode of the device to (1) the AAI mode with ventricular sensing and an active automatic mode commutation in response to an absence of the conduction disorder, and (2) a DDD mode with an inactive automatic mode commutation in response to a presence of the conduction disorder.

9. The method of claim 8, wherein the device includes a memory and the method further comprising setting an index, selectively as a function of the presence or the absence of the conduction disorder, and storing said index in said memory.

10. The method of claim 8, further comprising delaying the period of adaptation after detecting implantation.

11. The method of claim 8, wherein analyzing the atrio-ventricular conduction further comprises determining the presence of the conduction disorder when, over a predetermined period of time or a predetermined number of heart cycles, the number of commutations between the AAI mode and the DDD mode exceeds a first predetermined threshold.

12. The method of claim 11, wherein analyzing the atrio-ventricular conduction further comprises excluding from said predetermined period of time or said predetermined number of heart cycles, periods of the conduction disorder, phases of a sinusal tachycardia beyond a predetermined value of heart rate, and phases of exercise identified by means of a physiologic sensor.

13. The method of claim 8, wherein analyzing the atrio-ventricular conduction further comprises determining the presence of the conduction disorder when, over a predetermined period of time or a predetermined number of heart cycles, the percentage of paced ventricular cycles exceeds a second predetermined threshold.

14. The method of the claim 13, wherein analyzing the atrio-ventricular conduction further comprises excluding from said predetermined period of time or said predetermined number of heart cycles, periods of the conduction disorder, phases of a sinusal tachycardia beyond a predetermined value of heart rate, and phases of exercise identified by means of a physiologic sensor.

* * * * *